(12) United States Patent
Soll

(10) Patent No.: US 7,976,833 B2
(45) Date of Patent: Jul. 12, 2011

(54) OPHTHALMIC SURGICAL IRRIGATING SOLUTIONS CONTAINING HYALURONIDASE AND METHOD FOR PREVENTING POST-OPERATIVE INTRAOCULAR PRESSURE INCREASES

(75) Inventor: David B. Soll, Horsham, PA (US)

(73) Assignee: Aspen Biomedical Research, LLC, Ambler, PA (US)

( * ) Notice: Subject to any disclaimer, the term of this patent is extended or adjusted under 35 U.S.C. 154(b) by 714 days.

(21) Appl. No.: 11/548,076

(22) Filed: Oct. 10, 2006

(65) Prior Publication Data

US 2007/0137657 A1    Jun. 21, 2007

Related U.S. Application Data

(60) Provisional application No. 60/726,571, filed on Oct. 14, 2005.

(51) Int. Cl.
*A61K 38/46* (2006.01)
*A61K 31/74* (2006.01)

(52) U.S. Cl. .................... 424/78.04; 424/94.62; 435/201

(58) Field of Classification Search ................ 424/78.04, 424/94.62, 600; 435/201
See application file for complete search history.

(56) References Cited

U.S. PATENT DOCUMENTS 6,745,776 B2    6/2004    Soll
2005/0031697 A1 *  2/2005    Vehige et al. ................. 424/488

OTHER PUBLICATIONS

Takahashi et al., Arch Ophthalmology; 120:1348-1352 (2002).
Cameron et al., J Cataract Refract Surg.; 27:463-470 (2001).
Shimmura et al., Invest Ophthalmol Vis Sci.; 33:2904-2907 (1992).
Holst et al., Current Eye Research;12:359-365 (1993).
Miura, et al., Biochemistry & Molecular Biology International; 125-133 (1993).
Hiramoto, et al., Biol Pharm Bull.; 558-563 (1996).
Buratto et al., Viscoelastics in Ophthalmic Surgery, Slack Inc Publishings, (2000).
Mac Rae et al., Am J Ophthalmol.; 95:332-341 (1983).
Glasser et al., Arch Ophthalmol.; 104:1819-1824(1986).
Raitta et al., Acta Ophthalmol.; 66:544-551 (1988).
Berson et al., Am J Ophthalmol.; 95: 668-672 (1983).
Glasser, et al., Am J Ophthalmol.; 99:321-328 (1985).
Edelhauser et al., Arch Ophthalmol.; 96:516-520 (1978).
Araie et al., Invest Opth Vis Sci.; 29:1884-1887 (1985).
Whikehart et al., Current Eye Res.; 1:451-455 (1981).
Hodson et al., J. Physiol.; 263:563-577 (1976).
Hull et al., Invest Ophthalmol Vis Sci.; 16:883-892 (1977).
Barfort et al., Exp Eye Res.; 19:11-19 (1974).
Hodson et al., Invest Ophthalmol Vis Sci.; 16:589-591 (1977).
Mayes et al., Exp Eye Res.; 28: 699-707 (1979).
Chen et al., Transplantation; 57: 1778-1785 (1994).
Chen et al., Transplantation; 67: 800-808 (1999).
Halberstadt et al., Cryobiology; 43: 71-80 (2001).
Gonnering et al., Invest Ophthalmol Vis Sci.; 18:373-390 (1979).
Waring et. al., Ophthalmology; 89:531-590 (1982).
Harooni et al., Arch Ophthalmol; 116: 1218-1221 (1998).
Barany et al., Acta Phys, Scandinav.; 30: 240-248 (1953).
Hein et al., Ophthalmic Surg.; 17:731-734 (1986).
Physicians Desk Reference for Ophthalmic Medicines, pp. 12-13, 34th Edition, Thomson PDR, Montrale, New Jersey (2006).

* cited by examiner

*Primary Examiner* — Ruth A Davis
(74) *Attorney, Agent, or Firm* — Panitch Schwarze Belisario & Nadel LLP

(57) ABSTRACT

An ophthalmic irrigating solution containing hyaluronidase and an antioxidant is provided. The solution prevents a post-operative intraocular pressure rise when used during an ophthalmic surgical procedure, and also protects corneal endothelial cells. A method for preventing post-operative intraocular pressure increases in an eye during ophthalmic surgery involves irrigating an anterior chamber of the eye with an ophthalmic solution containing hyaluronidase and an antioxidant. Kits containing hyaluronidase and base medium solutions are also provided. The kits are designed such that the hyaluronidase and base medium solution are combined and administered together to an eye of a patient during or following an ophthalmic surgical procedure, such as cataract surgery, intraocular lens surgery, corneal transplant surgery, or glaucoma surgery. Administration of the components of the kit prevents an increase in post-operative intraocular pressure and also protects corneal endothelial cells.

10 Claims, No Drawings

OPHTHALMIC SURGICAL IRRIGATING SOLUTIONS CONTAINING HYALURONIDASE AND METHOD FOR PREVENTING POST-OPERATIVE INTRAOCULAR PRESSURE INCREASES

CROSS-REFERENCE TO RELATED APPLICATIONS

This application claims the benefit of U.S. Provisional Application No. 60/726,571, filed Oct. 14, 2005, the disclosure of which is incorporated herein by reference.

BACKGROUND OF THE INVENTION

The major structures of the eye are the sclera, cornea, iris, lens, vitreous, retina, and optic nerve. The function of the lens, which is located behind the iris, is to focus light onto the retina. The lens is mostly composed of water and proteins. The structure of the lens and the arrangement of the protein lens fibers allow light to pass through and focus on the retina, which senses the light and sends visual signals to the brain via the optic nerve. The transparency of the lens is essential for normal vision.

A cataract is a clouding or development of an opaque area in the lens. Most cataracts form as part of the aging process, but some are associated with congenital or systemic pathological conditions and others are related to ocular trauma. Cataracts are formed by the clumping of the proteins in the lens and the opacification that ensues, which hinders light transmission and normal vision.

At present, the only effective way to treat cataracts is to surgically remove the opaque lens. It is estimated that about 2.3 million cataract surgeries were performed in the United States in 2004, and the number of such procedures has been shown to increase by about 3% per year (Market Scope).

Currently, there are several operative procedures for removing cataracts: extracapsular cataract extraction, intracapsular cataract extraction, and phacoemulsification. In extracapsular cataract extraction, a large bulk of cataractus material is expressed from the eye through a moderately large incision. In contrast, in intracapsular cataract extraction, the entire cataract is removed from the eye in one piece.

Currently, phacoemulsification, a form of extracapsular cataract surgery, is the most common method of cataract removal in the United States and in many Western countries. In phacoemulsification, which is performed through a small incision, the cataractus lens material is ground up by ultrasonic energy and aspirated from the eye by suction. Most often, an intraocular lens is inserted in the patient's eye at the time of the cataract removal. This synthetic lens has clear optics and replaces the removed cataractus lens material.

While phacoemulsification and other forms of cataract surgery are considered to be safe surgical techniques, corneal endothelial damage can still be a serious complication. Excessive damage to the corneal endothelium can lead to irreversible decompensation of the cornea which results in corneal swelling (bullous keratopathy), pain, and loss of vision. Corneal, damage can be caused by shock wave injury, fluid flow turbulence injury, thermal injury, free-radical formation, and increased intraocular pressure (Takahashi et al., *Arch Ophthalmology;* 120:1348-1352 (2002); Cameron et al., *J Cataract Refract Surg.;* 27:463-470 (2001); Shimmuara et al., *Invest Ophthalmol Vis Sci.;* 33:2904-2907 (1992); Holst et al., *Current Eye Research;* 12:359-365 (1993)).

During phacoemulsification, hydroxyl radicals and hydrogen atoms are formed when the ultrasound energy in aqueous solution induces acoustic cavitations that cause gas bubbles to collapse, leading to the thermal dissociation of water and vapor into hydroxyl radicals and hydrogen atoms (Takahashi et al., *Arch Opthalmology;* 120:1348-1352 (2002); Cameron et al., *J Cataract Refract Surg.;* 27:463-470 (2001)). Such free radicals can inhibit the function of important cellular proteins, such as lactate dehydrogenase and creatine kinase, and induce strand breaks in DNA, resulting in endothelial damage (Miura, et al., *Biochemistry & Molecular Biology International;* 125-133 (1993); Hiramoto, et al., *Biol Pharm Bull.;* 558-563 (1996)).

Most Ophthalmic Viscosurgical Devices (OVDs) are polysaccharides of hyaluronic acid which are used during cataract surgery. OVDs protect and maintain the space and stability of the ocular structures during the surgical procedure (Buratto et al., *Viscoelastics in Ophthalmic Surgery,* Slack Inc Publishings, (2000)). However despite their advantages, the use of OVDs has been correlated with significant increases in postoperative intraocular pressure (Mac Rae et al., *Am J Ophthalmol;* 95:332-341 (1983), Glasser et al., *Arch Ophthalmol.;* 104:18198-1824 (1986); Raitta et al., *Acta Ophthalmol.;* 66:544-551 (1988)), which can lead to ocular damage. It has been hypothesized that the retained hyaluronic acid and other material from the OVDs block the outflow facility of the aqueous humor, resulting in an increase in intraocular pressure (Berson et al., *Am J Ophthalmol.;* 95: 668-672 (1983)).

Phacoemulsification and other cataract extracapsular removal procedures require the use of a balanced salt solution which is irrigated into the anterior chamber of the eye during the procedure. This irrigating solution maintains the shape of the eye, keeps the ultrasonic tip of the phacoemulsification unit, which is vibrating at approximately 40,000 cycles per second, cool, and assists in the elimination of cataractus lens particles in all types of extracapsular cataract surgery. During surgery, the irrigating solution is constantly flowed into the eye and aspirated out, thus maintaining an equilibrium pressure in the eye. More specifically, the tip of the phacoemulsification unit is connected via tubing to a bottle of balanced salt solution. The solution thus flows through the tip. Simultaneously, the center of the tip provides suction to remove the cataract material and salt solution, maintaining equilibrium. The flow is controlled via a foot pedal which is operated by the surgeon. It is common to leave some of the irrigating solution in the eye at the conclusion of the surgical procedure to maintain the shape of the eye.

Some commercially available intraocular irrigating solutions also help to protect corneal endothelial cells. For example, Balanced Salt Solution Plus (BSS PLUS®) (Alcon Laboratories, Inc., Fort Worth, Tex.) is an intraocular irrigating solution that has been demonstrated to reduce corneal endothelium damage during phacoemulsification (Glasser, et al., *Am J Ophthalmol.;* 99:321-328 (1985)). BSS PLUS® contains, in addition to various salts, glutathione, sodium bicarbonate, and dextrose. Glutathione is a natural antioxidant that serves as a free-radical scavenger and has been demonstrated to help protect the corneal endothelium and maintain corneal transparency (Edelhauser et al., *Arch. Ophthalmol.;* 96:516-520 (1978); Araie et al., *Invest Opth Vis Sci.;* 29:1884-1887 (1985); Whikehart et al., *Current Eye Res.;* 1:451-5 (1981)). Sodium bicarbonate functions as a buffer solution and dextrose acts as an energy source that can help maintain proper metabolism (Hodson et al., *J. Physiol.;* 263: 563-77 (1976); Hull et al., *Invest Ophthalmol Vis Sci.;* 16:883-892 (1977); Barfort et al., *Exp Eye Res.;* 19:11-19 (1974)).

Many surgeons prefer to use BSS PLUS® because it is, at present, the only intraocular irrigating solution which has undergone appropriate clinical evaluation for endothelial protection. However at a price range of $50-$60 per 500 ml bottle (with only about:40% of the bottle being utilized), the use of BSS PLUS® is very costly to the surgeon and patient care. The unused, discarded BSS PLUS® results in a loss of about $30 per procedure or $40,000 per year or more for an average surgical center.

A post-operative intraocular pressure rise during the first twenty-four hours after cataract surgery is common. Such a pressure rise is especially common when OVDs are used, since some of the OVD which is not aspirated from the eye blocks the trabecular meshwork. While post-operative pressure rises may also occur in the absence of OVDs, they are typically not as severe. For a typical patient, a normal intraocular pressure level is less than about 20 mm Hg gauge, and usually about 10 to about 18 mm Hg gauge. Following surgery, intraocular pressures as high as 40 mm Hg gauge are observed in some cases. In some patients, particularly those suffering from advanced glaucoma, intraocular pressure rises may be disastrous and result in visual loss. Specifically, the high pressure compromises circulation to the optic nerve, with subsequent death of retinal cells.

Current methods for relieving post-operative pressure increases in the eye include various types of eye drops, such as beta-adrenergic blocking agents, sympathomimetic agents, miotics, alpha II selective agents, carbonic anhydrase inhibitors, and prostaglandin agents, as well as systemic carbonic anhydrase inhibitors. Tables listing some of these agents appear in the *Physician's Desk Reference for Ophthalmology* 2006.

Such methods for relieving elevated intraocular pressure are often undesirable because of the side effects of many of these drugs. For example, systemic carbonic anhydrase inhibitors can cause lethargy and, in some instances, disorientation. Beta-blocker medications are contraindicated in patients with breathing problems or slow heart rates. Sympathomimetic drugs can cause an increase in blood pressure. Parasympathomimetic drugs can be associated with retinal detachments in eyes with peripheral retinal and retinovascular diseases. The above medications all work to lower intraocular pressure by either decreasing aqueous humor formation or increasing the amount of aqueous humor outflow (removal) from the anterior chamber. In some instances, if significant amounts of hyaluronic acid or a similar viscoelastic agent which is added during surgery are left in the eye and medications are not effective in lowering the intraocular pressure, it may be necessary to surgically aspirate them by performing a second surgical procedure which removes the retained OVD or other material. However, aspirating the remaining viscoelastic agent from a patient's anterior chamber subjects the patient to an additional operative procedure.

U.S. Pat. No. 6,745,776 of Applicant is directed to a method for reducing postoperative intraocular pressure in an eye. The method involves injecting a combination of hyaluronidase and hyaluronic acid into the anterior chamber of the eye at the appropriate time during an operative procedure. The hyaluronidase which is administered with the hyaluronic acid is provided in an amount effective to reduce the intraocular pressure to substantially pre-operative levels. However, such a method is performed only in conjunction with the administration of hyaluronic acid during surgery.

It would thus be desirable to find a better method of controlling post-operative intraocular pressure increases which would be effective and applicable in all types of ophthalmic surgeries. Preferably, such a method would also prevent endothelial cell damage by preventing such post-operative intraocular pressure rises.

SUMMARY OF THE INVENTION

An ophthalmic irrigating solution comprising hyaluronidase and an antioxidant is provided. The solution prevents a post-operative intraocular pressure rise when used during an ophthalmic surgical procedure, and also protects corneal endothelial cells.

A method for preventing a post-operative intraocular pressure increase in an eye comprises performing an ophthalmic surgical procedure on an eye and irrigating an anterior chamber of the eye with an ophthalmic solution comprising hyaluronidase and an antioxidant during the procedure. The resulting post-operative intraocular pressure in the eye is at a substantially pre-operative level.

A first kit according to the invention comprises a syringe containing hyaluronidase and a vial containing a base medium solution. The syringe and vial are so arranged that upon operation of the syringe to administer the hyaluronidase to a subject, the solution in the vial is aspirated into and mixes with the hyaluronidase, and the solution and hyaluronidase are administered together.

A second kit according to the invention comprises a vial containing hyaluronidase, a vial containing a base medium solution, and a syringe. The syringe and the vials are so arranged that the contents of the vials are aspirated into the syringe and administered to a subject together.

DETAILED DESCRIPTION OF THE INVENTION

According to the present invention, an ophthalmic irrigating solution is provided which comprises hyaluronidase and an antioxidant. The preferred concentration of hyaluronidase in the solution is a concentration which is effective to control intraocular pressure rises, and is preferably about 0.1 to about 25 units hyaluronidase per ml of irrigating solution.

One highly preferred form of hyaluronidase is the Wyadase™ preparation, formerly commercially available from Wyeth-Ayerst. Hyaluronidase is currently available from Amphastar as Amphadase™. These preparations are sodium chloride solutions of hyaluronidase. Alternatively, hyaluronidase is also commercially available as Vitrase™ from ISTA Pharmaceuticals, in which it is provided as a powder which is designed to be diluted with sodium chloride solution prior to use. Any highly purified form of hyaluronidase which is known or to be developed may be used in the present invention. Additionally, any type of pure non-antigenic preparation of hyaluronidase may be used in this invention as well.

The irrigating solution also contains at least one antioxidant. As previously explained, the primary free-radicals formed during phacoemulsification are hydroxyl radicals. These free radicals can inhibit the function of important cellular proteins, such as lactate dehydrogenase and creatine kinase, and induce strand breaks in DNA, resulting in endothelial damage. In order to avoid such events, it is most preferred that the antioxidant be one which has been demonstrated to specifically capture hydroxyl radicals, also referred to as a free radical scavenger. Preferably, the antioxidant is a "strong" antioxidant, that is, one with demonstrated high potency. The antioxidant is included in the irrigating solution to prevent corneal endothelial cell loss. A list of preferred antioxidants and preferred concentration ranges is shown in Table 1; the irrigating solution according to the invention preferably contains at least one of these antioxidants. However, other antioxidants which are known or to be developed may also be included in the irrigating solution according to the invention.

TABLE 1

Preferred Antioxidants for Use in Irrigating Solution

| Antioxidant | Preferred Concentration |
| --- | --- |
| Ascorbic Acid | 50 μM-2 mM |
| Carnosine or derivative thereof | 10 μM-1000 μM |
| Fisetin | 1 mM-20 mM |
| Gallic acid | 10 μM-1000 μM |
| Hydralazine | 5 μM-1 mM |
| Morin | 100 μM-10 mM |
| Quercetin | 10 μM-1000 μM |
| Glutathione or Thiol-containing antioxidant | 500 μM-1000 μM |
| Trolox | 100 μM-1000 μM |

The solution also preferably comprises a base medium composed of an aqueous solution of inorganic salts which will maintain the viability of cells as well a prevent endothelial cell damage during a surgical procedure. The inorganic salts provide an ionic balance that will help control the ion and water distribution between the intracellular and extracellular compartments during the surgical procedure. The components and preferred concentration ranges of a preferred base medium are shown in Table 2. However, a base medium containing alternative, additional, or fewer salts which would fulfill a similar function would also be within the scope of the invention.

TABLE 2

Preferred Base Medium Composition

| Inorganic Salt | Preferred Concentration (mg/L) |
| --- | --- |
| Calcium Chloride ($CaCl_2$) | 100-200 |
| Magnesium Chloride ($MgCl_2$) | 100-200 |
| Magnesium Sulfate ($MgSO_4$) | 100-200 |
| Potassium Chloride (KCl) | 400-500 |
| Potassium Phosphate ($KH_2PO_4$) | 50-100 |
| Sodium Bicarbonate ($NaHCO_3$) | 300-400 |
| Sodium Chloride (NaCl) | 8000-8500 |
| Sodium Phosphate ($Na_2HPO_4$) | 30-50 |

A further preferred component in the irrigating solution is at least one component which functions as an energy source and controls energy metabolism. Energy metabolism is involved in the regulation of corneal deturgesence, the mechanism by which the stroma of the cornea remains dehydrated. The plasma membrane of corneal endothelial cells contains endothelial pumps that catalyze the movement of ions from the stroma to the aqueous humor. An osmotic gradient is created that draws water out of the stroma (Hodson et al., *Invest Ophthalmol Vis Sci.;* 589-591 (1977); Mayes et al., *Exp Eye Res.;* 28: 699-707 (1979)). Thus, a steady source of ATP is required to provide the energy needed to maintain the pump function. Preferred energy sources are dextrose, which has been shown to support mitochondria metabolism and ATP production, and β-hydroxybutyrate, which has been demonstrated to support aerobic respiration and reduce lactate production (Chen et al., *Transplantation;* 57: 1778-1785 (1994); Chen et al., *Transplantation;* 67: 800-808 (1999)). ATP and precursors thereof would also be appropriate for pump maintenance and may be included as well in the inventive solution.

The preferred concentration of energy source is determined by the specific compound which is utilized. For example, the preferred concentration of dextrose is about 1 to about 10 mM, whereas the preferred concentration of β-hydroxybutyrate is about 0.1 to about 25 mM. If ATP or a precursor thereof is used, it is preferably included at a concentration of about 1 to about 25 mM. However, the specific concentration of a particular component in energy production or energy source may be determined by routine experimentation.

Finally, the solution preferably contains at least one component to assist in maintaining cell density and/or viability. Maintaining cell density is very important. Since corneal cells are essentially nonproliferative cells, there is no regenerative pathway to induce repair after endothelial damage. The preferred component for maintaining cell density and/or cell viability is high molecular weight dextran, which has been demonstrated to preserve the cell density of porcine cornea endothelial cells (Halberstadt et al., *Cryobiology;* 43: 71-80 (2001)) and to increase cell viability of bovine endothelial cells. The solution preferably contains high molecular weight dextran, more preferably dextran having a molecular weight of about 2,000,000 Daltons. However, for use in the invention, the term "high molecular weight dextran" encompasses dextran having a molecular weight of at least about 500,000 Daltons. It is presently preferred to utilize water soluble dextran fractions so that the resulting irrigating solution will be homogeneous. The high molecular weight dextran is preferably present in the solution at a concentration of about 0.5 to about 10 weight %, depending on the desired viscosity of the resulting solution. In addition to or instead of high molecular weight dextran, other compounds which are known or to be developed which would provide similar effects would also be applicable for inclusion in the inventive irrigating solution.

A presently preferred irrigating solution according to the invention contains hyaluronidase, the base medium in Table 2, an antioxidant (such as those in Table 1), β-hydroxybutyrate or dextrose, ATP or a precursor thereof, and high molecular weight dextran.

It is also within the scope of the invention to combine hyaluronidase with a commercially available irrigating solution prior to or during the operative procedure in order to provide the eye surgeon with an enhanced irrigating solution which will prevent increases in postoperative intraocular pressure. For example, BSS PLUS®, described previously, contains a base medium (sodium chloride, potassium, chloride, dibasic sodium phosphate, sodium bicarbonate, calcium chloride, and magnesium chloride), an energy source (dextrose), and an antioxidant (oxidized glutathione). Therefore, combination of hyaluronidase with BSS PLUS® would yield an enhanced irrigating solution which would simultaneously protect corneal endothelial cells and prevent an increase in intraocular pressure following surgery.

The pH range of the corneal endothelium has been reported to be 6.8-8.2 (Gonnering et al., *Invest Ophthalmol Vis Sci.;* 18:373-390 (1979); Waring et. al.; *Ophthalmology;* 89:531-590 (1982)). Accordingly, the irrigating solution according to the invention preferably has a pH of about 6.8 to about 9, more preferably about 6.8 to about 8.2. It is preferred that the solution be appropriately buffered to maintain such a physiological pH at atmospheric conditions. Appropriate buffers are well known to those skilled in the art.

It has been shown that corneal endothelial cells function properly within the osmotic pressure range of 200-400 mOsm (Waring, et. al., *Ophthalmology;* 89:531-590 (1982)). Therefore, the preferred osmotic pressure of the irrigating solution according to the invention is about 300 to about 350 mOsm. The osmolality may be controlled and maintained by appropriate concentrations of the inorganic salts in the base medium.

The irrigating solution according to the invention is not limited to use in cataract surgery, but may be appropriate for use during a variety of ophthalmic surgical procedures. The terms "ophthalmic surgical procedure" and "operative procedure" may be understood to mean any operation or surgical procedure generally performed on an eye during which intraocular pressure increases naturally or is induced, such as cataract surgery, intraocular lens surgery, corneal transplant surgery, glaucoma surgery, or the like.

The administration of such a solution during surgical procedures may be performed by known methods, such as the continuous irrigation and aspiration of the solution into the eye during surgery, as previously described. Alternatively or additionally, the solution may be separately instilled or injected into the anterior chamber through a needle or cannula attached to a syringe at the conclusion of or immediately following the surgical procedure to inflate the globe. Such an injection may also be considered to be irrigation of the anterior chamber. Further, the solution according to the invention may be topically applied via a dropper type bottle or dripped from a syringe onto the external surface of the eye to maintain wetness during, surgery. The presence of hyaluronidase in the solution will prevent post-operative intraocular pressure rises, as explained below.

The concentration of hyaluronidase in the irrigating solution, preferably about 0.1 to about 25 units per ml of solution, is selected so that the amount of hyaluronidase which is administered to the eye during the surgical procedure will be sufficient to prevent post-operative intraocular pressure rises, that is, to maintain the post-operative pressure at a substantially pre-operative level.

The irrigating solution according to the invention is effective at controlling or preventing post-operative intraocular pressure rises as follows. Hyaluronic acid is a natural, high molecular weight, highly viscous polymer consisting of alternating acetylglycosamine and glucuronic acid units. This acid is found in the trabecular meshwork, the main drainage area for the aqueous humor fluid in the eye. It has been shown that the injection of hyaluronidase into the anterior chamber of animal and human eyes breaks down the bonds uniting the molecules of hyaluronic acid in the trabecular meshwork, thereby relieving pressure, enhancing the outflow of aqueous humor and preventing a rise in intraocular pressure (Harooni et al., *Arch Ophthalmol;* 116: 1218-1221 (1998); Barany et al., *Acta Phys. Scandinav.;* 30; 240-248 (1953); Hein et al., *Ophthalmic Surg.;* 17:731-734 (1986)). The solution according to the invention will thus reduce post-operative corneal swelling and maintain endothelial cell viability.

The presence of the antioxidant provides a solution which will neutralize free radicals that are generated during surgery. The antioxidant is thus protective for corneal endothelial cells and prevents undesirable corneal endothelial cell loss. In other words, there is less endothelial cell loss than would have occurred in the absence of an antioxidant, functioning as a free radial scavenger.

In so me cases, it may not be possible to completely prevent post-operative intraocular pressure rises. However, the irrigating solution according to the invention will still minimize such pressure rises. Ideally, the post-operative intraocular pressure will be maintained at a substantially pre-operative level.

According to the invention, a method for preventing post-operative intraocular pressure rises is also provided The method comprises performing an, ophthalmic surgical procedure (such as those procedures listed above) on an eye and irrigating the anterior chamber of the eye with an ophthalmic irrigating solution comprising hyaluronidase and an antioxidant during the procedure. The solution may be administered by known methods as previously described, including continuous irrigation and aspiration, instillation or injection into the anterior chamber, and topical administration to external eye surfaces. The resulting post-operative intraocular pressure in the eye is at a substantially pre-operative level and there is less corneal endothelial cell loss than would have occurred in the absence of such an antioxidant containing solution.

The method may further comprise preparing the ophthalmic irrigating solution containing hyaluronidase, such as by combining hyaluronidase and optionally an antioxidant with a known irrigating solution or base medium solution as previously described. The solution may also contain an energy source, ATP or a precursor thereof, and/or a composition for maintaining cell density and/or cell viability. The combination may be performed prior to administration or substantially contemporaneously with administration. For example, a known irrigating solution or base medium solution may be aspirated into a syringe and injected into a vial containing hyaluronidase and optionally an antioxidant. Mixing the contents will result in a new solution containing hyaluronidase and an antioxidant, which may then be aspirated and administered to the patient as described previously during or following the surgical procedure. Alternatively, the hyaluronidase may be provided in a syringe, which is then used to aspirate the known irrigating solution or base medium solution and an antioxidant. The resulting hyaluronidase- and antioxidant-containing solution, in the syringe, may then be administered to the patient as previously described. The hyaluronidase and antioxidant may also be administered after or simultaneously with the known irrigating solution, such as in the irrigating tubing used during surgery.

Any known surgical irrigating solution would be appropriate for combination with hyaluronidase in such a manner. Such methods would allow a surgeon to improve a known irrigating solution or base medium solution by providing the benefits of hyaluronidase for preventing increases in intraocular pressure following surgery without necessitating the administration of a separate medication during or following surgery. Including an antioxidant will also help protect corneal endothelial cells.

The hyaluronidase in the vial or syringe may be provided in powder, compressed pellet, or lyophilized form. Powdered, lyophilized, and compressed pellet forms of hyaluronidase are particularly attractive since they may be easily provided in a syringe or vial (or in an individual blister-pack, for example) in predetermined amounts and are shelf stable for prolonged periods of time and easy to handle. In particular, pellets containing various weights of hyaluronidase may be provided to a surgeon and the surgeon will be easily able to select the desired weight of hyaluronidase for dissolving in the base medium solution or irrigating solution depending on the particular patient or operative procedure.

As previously explained, current methods of relieving postoperative intraocular pressure include aspiration of the viscoelastic agent, such as hyaluronic acid, and the use of medications such as, eye drops and/or pills. However, these methods have significant drawbacks. For example, medications have side effects and many cataract patients, as well as other eye surgical patients, are in the older age group and cannot tolerate medications well. Also, in some instances it may be necessary to aspirate much of the viscoelastic agent, such as hyaluronic acid, which may have been left in the patient's eye. In many situations it is not advisable to subject an elderly patient to this type of secondary surgical procedure.

In contrast, the method of the present invention not only has significant advantages, but also has no negative side effects on the patient or deleterious effects on the outcome of the operative procedure. As the hyaluronidase, which is added to the eye as part of the irrigating solution, relieves the intraocular pressure, it may not be necessary to aspirate all of the hyaluronic acid or other hyaluronic-containing viscoelastic agents from the treated eye. Eliminating the complete or partial aspiration makes the operative procedure simpler and safer since there is less manipulation inside the eye, which could have an adverse effect on the cells within the eye. The surgery is also of shorter duration. Furthermore, because the hyaluronidase is added to the eye as part of the surgical procedure to improve outflow of aqueous humor though the trabecular meshwork, no additional procedure or medication is needed to relieve the intraocular pressure. Experiments have shown that the viscoelastic properties of the hyaluronic acid during the surgical procedure are not adversely affected by the presence of hyaluronidase. The hyaluronidase works to de-polymerize the hyaluronic acid such that even if none or only some of it is aspirated, it will be broken down and not cause a pressure rise in the eye. Finally, there are no known side effects associated with the administration of hyaluronidase.

In some cases, it may be advisable to leave a viscoelastic agent such as Healon™, Viscoat™, or other space-occupying substances in the anterior chamber of the eye at the conclusion of surgery. This is especially true in cases of a positive pressure eye, when the intraocular contents tend to come forward and press against the posterior surface of the cornea. If this occurs in an eye with a synthetic intraocular lens in place, pressure on the corneal endothelium can cause significant damage to the cells, resulting in subsequent corneal swelling, opacification, and decreased vision. A method for decreasing elevated intraocular pressure is thus necessary.

Traditionally, if a patient's intraocular pressure is significantly elevated at the conclusions of the operative procedure, the patient is given large doses of carbonic anhydrase inhibitors and/or topical eye drops, such as beta blockers and alpha II agonists, in order to decrease aqueous formation and/or to increase aqueous outflow. These agents all have significant side effects and, in some instances, are contraindicated in patients with various types of medical conditions, such as breathing problems, heart disease or high blood pressure. Many cataract patients, as well as other eye surgical patients, are in the older age group and cannot tolerate medications well. However, the use of hyaluronidase in these situations will eliminate the necessity of giving these patients such drugs. The use of hyaluronidase may be particularly desirable in some cases of newer implantable refractive lenses, when the patient's normal lens is left in the eye and in which minimal intraocular manipulation is desirable in order to prevent damage to the patient's normal lens so that all of the viscoelastic agent cannot be safely removed.

This invention also relates to kits which may be utilized by an eye surgeon during or following surgery. A first kit according to the invention comprises a syringe containing hyaluronidase in powder, lyophilized, compressed pellet, or solution form and a vial containing a base medium solution. The base medium solution is composed of an aqueous solution of inorganic salts, as previously described. In preferred embodiments, the vial also contains at least one antioxidant, at least one component which functions as an energy source and controls energy metabolism, and/or at least one component to assist in maintaining cell density and/or cell viability. Preferred components have been previously described.

The syringe and vial are so arranged that upon operation of the syringe to administer hyaluronidase to a subject, the base medium solution (and optionally other components) is aspirated into and mixes with the hyaluronidase, such that the hyaluronidase is dissolved in the solution and the hyaluronidase containing solution is administered to the eye. Specifically, in use, an eye surgeon will aspirate the solution into the syringe containing the hyaluronidase in solution, powder, compressed pellet, or lyophilized form. The hyaluronidase will then mix with and/or dissolve in the solution. Some or all of the resulting mixture may then be administered during and/or at the conclusion of the ophthalmic surgical procedure, as previously described, thus providing the surgeon with a straightforward, way to administer a solution containing hyaluronidase and other favorable components simultaneously. Instructions for utilization of the kit and a filter for the syringe may also be included. Such a filter may be connected to the syringe after aspirating the base medium solution but prior to administration to the patient to ensure that the mixture which is administered is completely free of particulates.

The syringe containing the hyaluronidase containing solution may be used during and/or following a surgical procedure. For example, the solution may be instilled or injected into the anterior chamber thru a needle or cannula attached to the syringe containing the solution. As previously explained, this irrigation of the anterior chamber will also serve to inflate the globe. Alternatively, the solution may be topically applied to the external surface of the eye from the syringe to maintain wetness during or following surgery.

A second kit according to the invention comprises a syringe, a vial containing hyaluronidase (in powder, lyophilized, compressed pellet, or solution form), and a vial containing a base medium solution as previously described. In a preferred embodiment, the vial also contains at least one antioxidant, at least one component which functions as an energy source and controls energy metabolism, and/or at least one component to assist in maintaining cell density and/or cell viability. In use, the surgeon would preferably aspirate the base medium solution (and optionally other components) into the syringe and inject it into the vial containing the hyaluronidase, thereby forming a new solution.

Alternatively, the hyaluronidase in compressed pellet form may be separately packaged, such as in an individual blister pack, for example, rather than contained in a vial. In use, the surgeon would open the blister pack, add the hyaluronidase pellet to the vial containing the base medium solution, and shake the vial to form a solution containing hyaluronidase.

In either case, the hyaluronidase solution may then be aspirated into the syringe (or into a second syringe, if desired), and some or all administered to the eye during and/or at the conclusion of the surgical procedure, as previously described. Instructions for utilization of the kit and a filter for the syringe may also be included. When using this kit, the filter would preferably be connected to the syringe after the combined hyaluronidase/base medium solution has been aspirated into the syringe, but prior to administering the solution to the eye of the patient.

Syringes, vials, and pellets which are included in the inventive kits may contain different amounts of hyaluronidase so that when the diluent is aspirated into the syringe, injected into the vial containing hyaluronidase, or combined with a hyaluronidase pellet, the concentration of hyaluronidase in the resulting solution will be in the preferred range of about 0.1 to about 25 units per ml. For example, if a dosage of 15 units hyaluronidase/ml is desired, a syringe containing 22.5 units of solid hyaluronidase would be utilized. In use, 1.5 ml of base medium solution may be aspirated into the syringe, forming a solution having a hyaluronidase concentration of 15 units/ml. The appropriate amount of this solution (typically about 20 to about 65%) may be then injected into the anterior chamber at the conclusion of the surgical procedure. Alternatively, if the hyaluronidase in the syringe is provided in solution, it must be of the appropriate concentration such that combination with the base medium solution will result in the final desired concentration for injection.

The hyaluronidase is administered to the eye in an amount effective to maintain the intraocular pressure at a substantially pre-operative level, or slightly lower. This effective amount of hyaluronidase depends on the particular operative procedure and the surgeon's judgment. One skilled in the art will thus be able to determine by routine experimentation the necessary amount of hyaluronidase which should be administered, based on the particular patient and procedure. In particular, the effective amount of hyaluronidase for most anterior segment procedures, cataract surgery, intraocular lens surgery, corneal, transplant surgery and glaucoma surgery is about 0.1 units per ml to about 25 units per ml, and more preferably about 15 units per ml of solution injected into the anterior chamber of the eye. The actual amount of hyaluronidase which is administered will be dependent on the particular preparation which is utilized. For example, commercially available Vitrase™ has a hyaluronidase concentration of 200 units/ml, and Wyadase™ and Amphadase™ have hyaluronidase concentrations of 150 units/ml. Using these preparations, in order to administer the desired hyaluronidase concentration of about 0.1 to about 25 units/ml, a surgeon would administer about 0.5 to about 170 µl of hyaluronidase solution in combination with the appropriate amount of base medium solution or known irrigating solution. Alternatively, when the hyaluronidase is provided in solid form, an appropriate weight may be diluted with the base medium solution or known irrigating solution in order to achieve the desired concentration for administration to the eye.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

I claim:

1. A method for preventing a post-operative intraocular pressure increase in an eye, the method comprising performing an ophthalmic surgical procedure on an eye and irrigating an anterior chamber of the eye with an ophthalmic solution comprising hyaluronidase, β-hydroxybutyrate, and an antioxidant during the procedure such that a post-operative intraocular pressure in the eye is at a substantially pre-operative level.

2. The method according to claim 1, wherein the pre-operative level of intraocular pressure is less than about 20 mm Hg gauge.

3. The method according to claim 1, wherein the surgical procedure is selected from the group consisting of cataract surgery, intraocular lens surgery, corneal transplant surgery, and glaucoma surgery.

4. The method according to claim 1, wherein the solution comprises about 0.1 to about 25 units hyaluronidase per ml of the solution.

5. The method according to claim 1, further comprising continuously irrigating and aspirating the solution into and from the eye during the surgical procedure.

6. The method according to claim 1, wherein the method prevents endothelial cell damage in the eye during the surgical procedure.

7. The method according to claim 1, further comprising injecting the solution into an anterior chamber of the eye during or following the surgical procedure.

8. The method according to claim 1, further comprising topically applying the solution to a surface of the eye during or following the surgical procedure.

9. The method according to claim 1, further comprising preparing the irrigating solution by combining hyaluronidase, β-hydroxybutyrate, and an antioxidant with a solution comprising a base medium.

10. The method according to claim 9, wherein the solution further comprises at least one component selected from the group consisting of an energy source, ATP and precursors thereof, and a component for maintaining cell density and/or cell viability.

* * * * *